United States Patent
Gooding et al.

(10) Patent No.: US 8,323,617 B2
(45) Date of Patent: *Dec. 4, 2012

(54) TREATMENT OF ARTHRITIS AND OTHER MUSCULOSKELETAL DISORDERS WITH CROSSLINKED HYALURONIC ACID

(75) Inventors: Tamera B. Gooding, Jamaica Plain, MA (US); Stephen J. Kennedy, Hudson, NH (US); Charles H. Sherwood, Sudbury, MA (US)

(73) Assignee: Anika Therapeutics, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/165,196

(22) Filed: Jun. 21, 2011

(65) Prior Publication Data

US 2011/0312912 A1 Dec. 22, 2011

Related U.S. Application Data

(62) Division of application No. 11/638,307, filed on Dec. 13, 2006.

(60) Provisional application No. 60/751,237, filed on Dec. 14, 2005, provisional application No. 60/751,381, filed on Dec. 14, 2005, provisional application No. 60/751,414, filed on Dec. 14, 2005.

(51) Int. Cl.
| | |
|---|---|
| *A61K 51/00* | (2006.01) |
| *A61K 31/715* | (2006.01) |
| *A61K 31/56* | (2006.01) |
| *A61M 36/14* | (2006.01) |
| *A01N 43/04* | (2006.01) |
| *A01N 45/00* | (2006.01) |

(52) U.S. Cl. .......... 424/1.73; 514/54; 514/171; 514/177
(58) Field of Classification Search .................. 424/1.73; 514/54, 171, 177
See application file for complete search history.

(56) References Cited

U.S. PATENT DOCUMENTS

| | | |
|---|---|---|
| 4,141,973 A | 2/1979 | Balazs |
| 4,801,619 A | 1/1989 | Lindblad et al. |
| 4,808,576 A | 2/1989 | Schultz et al. |
| 5,079,236 A | 1/1992 | Drizen et al. |
| 5,128,326 A | 7/1992 | Balazs et al. |
| 5,143,724 A | 9/1992 | Leshchiner et al. |
| 6,288,043 B1 | 9/2001 | Spiro et al. |
| 6,527,760 B1 | 3/2003 | Vad |
| 6,699,471 B2 | 3/2004 | Radice et al. |
| 6,979,679 B2 | 12/2005 | Marcum |
| 7,157,080 B2 | 1/2007 | Radice et al. |
| 2004/0058858 A1 | 3/2004 | Hu |
| 2005/0136122 A1 | 6/2005 | Sadozai et al. |

FOREIGN PATENT DOCUMENTS

| | | |
|---|---|---|
| EP | 0416250 A2 | 3/1991 |
| WO | WO-02/09792 A1 | 2/2002 |
| WO | WO-02/068383 A2 | 9/2002 |
| WO | WO-2004/022603 A1 | 3/2004 |
| WO | WO-2004/034980 | 4/2004 |
| WO | WO-2006/012492 | 2/2006 |

OTHER PUBLICATIONS

Wen, D.Y. (2000) Intra-articular Hyaluronic Acid Injections for Knee Osteoarthritis. American Family Physician, vol. 62, p. 565-570.*
Gaffney, K., Ledingham, J., Perry, J.D. (1995) Intra-articular triamcinolone hexacetonide in knee osteoarthritis: factors influencing the clinical response. Annals of the Rheumatic Diseases, vol. 54, p. 379-381.*
Courtney, P., Doherty, M. (2005) Joint aspiration and injection. Best Practice & Research Clinical Rheumatology, vol. 19, No. 3, p. 345-369.*
"Hyaluronate Sodium (Systemic)" from Drugs.com [online], [retrieved Dec. 5, 2011]. Retrieved from the internet http://www.drugs.com/mmx/hyalgan.html> Published Jul. 25, 2001.*
"Hyaluronate Sodium Derivative (Systemic)" from Drugs.com [online], [retrieved Dec. 5, 2011]. Retrieved from the internet http://www.drugs.com/mmx/synvisc.html> Published Oct. 15, 1998.*
Remington's The Science and Practice of Pharmacy, 19th Edition, editor Alfonso R. Gennaro, published by Mack Publishing Company (1995) p. 1463-1482.*
Altman, R.D., et al., "Efficacy and safety of a single intra-articular injection of non-animal stabilized hyaluronic acid (NASHA) in patients with osteoarthritis of the knee," OsteoArthritis and Cartilage (2004), vol. 12, pp. 642-649.
Arnold, W., et al., "Viscosupplementation: Managed care issues for osteoarthritis of the knee," J. of Managed Care Pharmacy, Supplement, May 2007, vol. 13, No. 4, 28 pgs.
Brandt, K. D., et al., "Intraarticular injection of hyaluronan as treatment for knee osteoarthritis," Arthritis & Rheumatism, vol. 43, No. 6, Jun. 2000, pp. 1192-1203.

(Continued)

*Primary Examiner* — Scarlett Goon
(74) *Attorney, Agent, or Firm* — Wilmer Cutler Pickering Hale & Dorr LLP.

(57) ABSTRACT

A method of treating a subject having a musculoskeletal disorder includes administering to a subject's articular site in need thereof an effective amount of a hyaluronic acid (HA) composition. In one embodiment, the HA composition includes an HA derivative, wherein carboxyl functionalities of the hyaluronic acid derivative are each independently derivatized to include an N-acylurea or O-acyl isourea, or both N-acylurea and O-acyl isourea. In another embodiment, the HA composition includes a crosslinked HA gel that is prepared by reacting an uncrosslinked HA with a biscarbodiimide in the presence of pH buffer in a range of between about 4 and about 8. The composite can optionally include at least one second bioactive agent other than the HA derivative, such as a steroid.

9 Claims, No Drawings

OTHER PUBLICATIONS

Conrozier, T., et al., "Factors predicting long-term efficacy of hylan GF-20 viscosupplementation in knee osteoarthritis," Joint Bone Spine 70 (2003), pp. 128-133.
European Examination Report, European Patent Application No. 06847587.0, dated Feb. 10, 2009 (4 pages).
Examination Report issued for European Appl. No. 06847587.0 dated Feb. 10, 2009 (1 page).
George, E., "Intra-articular hyaluronan treatment of osteoarthritis," Ann Rheum Dis 1998, vol. 57, pp. 637-640.
Huskisson, E.C., et al., "Hyaluronic acid in the treatment of osteoarthritis of the knee," Rheumatology, 1999, vol. 38, pp. 602-607.
Lussier, A., et al., "Viscosupplementation with hylan for the treatment of osteoarthritis: finds from clinical practice in canada," J. of Rheumatology, 1996, vol. 23 No. 9, pp. 1579-1585.
Peyron, J. G., "Intraarticular hyaluronan injections in the treatment of osteoarthritis: state of the art review," J. of Rheumatology, 1993 vol. 20, Supp. 39, pp. 10-15.
Rees, J. D., et al., "Systemic reaction to viscosupplementation for knee osteoarthritis," Rheumatology 2001, vol. 40, pp. 1425-1426.
Rydell, N., et al., "Effect of intra-articular injection of hyaluronic acid on the clinical symptoms of osteoarthritis and on granulation tissue formation," Clinical Orthpaedics and Related Research, No. 80, Oct. 1971, pp. 25-32.
Soltes, L. and Medichi, R. "Molecular characterization of two host-guest associating hyaluronan derivatives," Biomed. Chroma., 17: 376-384 (2003).
Soltes, L. et al., "Associating Hyaluronan Derivatives: A Novel Horizon in Viscosupplementation of Osteoarthritic Joints," Chem. & Biodiv., vol. 1: 468-472 (2004).
Weiss, C., et al., "Clinical studies of the intraarticular injection of healon® (sodium hyaluronate) in the treatment of osteoarthritis of human knees," Osteoarthritis Symposium, 1981 by Grune & Stratton, Inc., pp. 143-144.
Wobig, M., et al., "Viscosupplementation with hylan G-F 20: A 26-week controlled trial of efficacy and safety in the osteoarthritic knee," Clinical Therapeutics, vol. 20, No. 3, 1998, pp. 410-423.

* cited by examiner

TREATMENT OF ARTHRITIS AND OTHER MUSCULOSKELETAL DISORDERS WITH CROSSLINKED HYALURONIC ACID

This application is a division of U.S. patent application Ser. No. 11/638,307, filed Dec. 13, 2006, which claims the benefit of priority to U.S. Provisional Patent Application Ser. Nos. 60/751,237, 60/751,381 and 60/751,414, all filed on Dec. 14, 2005, the entire disclosures of which are incorporated by reference in their entity.

BACKGROUND OF THE INVENTION

Arthritis is a musculoskeletal disorder which is one of the leading causes of disability in the United States of America and the rest of the world. In particular, osteoarthritis (OA) is one of the most frequent articular pathologies in humans, and a common condition leading to total joint arthroplasty (artificial joint placement) in elderly individuals. Osteoarthritis is typically characterized by degenerative changes in the surface of the articular cartilage which results in cartilage thinning. It usually presents a pain, which worsens with exercise. Commonly affected joints are the knee, hips, spine, ankles, shoulders, fingers and toes.

To date, no therapies have been shown to unequivocally alter the clinical course of OA. The primary treatment goals are thus so far to relieve the OA symptoms, i.e., adequate pain relief and maintain mobility. Current treatments for OA include use of non-steroidal anti-inflammatory drugs (NSAIDs) and intra-articular injections of corticosteroids. Prolonged use of NSAIDs can, however, lead to gastric ulcers, kidney damage, hearing loss and even inhibit cartilage formation. Corticosteroids provide short-term improvement of OA symptoms with quick onset of pain relief in the arthritic joints but their repeated use is limited due to the known side-effects of steroids.

Therefore, there is a need for development of new therapies for treating arthritis (e.g., osteoarthritis) that overcome or minimize the above-mentioned problems.

SUMMARY OF THE INVENTION

The invention generally is directed to a method of treating a subject having a musculoskeletal disorder with a hyaluronic acid (HA) derivative, such as a crosslinked HA gel.

In one embodiment, the method includes administering to a subject's articular site in need thereof an effective amount of an hyaluronic acid composition. The hyaluronic acid composition includes a hyaluronic acid derivative, wherein carboxyl functionalities of the hyaluronic acid derivative are each independently derivatized to include an N-acylurea or O-acyl isourea, or both N-acylurea and O-acyl isourea.

In another embodiment, the method includes co-administering to an articular site of the subject an effective amount of a hyaluronic acid derivative as described above, and an effective amount of at least one second bioactive agent other than the HA derivative. The bioactive agent includes at least one member selected from the group consisting of cells, nucleic acids, proteins, antibodies, peptides and pharmaceuticals, such as growth factors, antibiotics, analgesics, anesthetics, steroidal and non-steroidal anti-inflammatory agents, chondroregenerative agents, chondroprotective agents, matrix metalloproteinase (MMP) inhibitors, tissue inhibitors of matrix metalloproteinase (TIMP), bone protective agents, bone regenerating agents, bone anabolic agents, bone resorption inhibitors, and bone osteoclast inhibiting agents.

In yet another embodiment, the present invention is directed to a method of treating a subject having a musculoskeletal disorder that includes the step of inserting a needle into a subject's articular site in need thereof, wherein the needle is coupled to a syringe loaded with a HA composition as described above. Force is applied to the syringe, whereby at least a portion of the HA composition is delivered to the articular site.

The present invention also provides a method of treating a subject having a musculoskeletal disorder with an effective amount of an HA composition including a crosslinked hyaluronic acid (HA) gel that is prepared by reacting an uncrosslinked HA with a biscarbodiimide in the presence of a pH buffer in a range of between about 4 and about 8 is also included in the invention.

With the present invention, the residence time of HA in the joints can be improved, providing longer therapeutic effect, which in turn can reduce the frequency of administration, e.g., intra-articular injections, in OA patients, but yet effecting the efficiency and safety typical of uncrosslinked HA. In particular, co-therapy of the crosslinked HA in combination with a corticosteroid can provide rapid pain relief due to the presence of the corticosteroid, and prolonged pain relief due to the presence of the crosslinked HA.

DETAILED DESCRIPTION OF THE INVENTION

The foregoing and other objects, features and advantages of the invention will be apparent from the following more particular description of preferred embodiments of the invention.

The method of the invention which employs a hyaluronic acid derivative, such as a crosslinked hyaluronic acid gel, can treat a subject having a musculoskeletal disorder, such as arthritis. In a preferred embodiment, the musculoskeletal disorder is osteoarthritis (OA).

As used herein, the term "hyaluronic acid derivative" means hyaluronic acid derivatized in that carboxyl functionalities of the hyaluronic acid (HA) (a portion or all) are each independently derivatized to include an N-acylurea or O-acyl isourea, or both N-acylurea and O-acyl isourea. As used herein, hyaluronic acid, and any of its salts which are often referred to as "hyaluronan"_(e.g., sodium, potassium, magnesium, calcium or ammonium salts) are represented by the term "HA." Typically, HA comprises disaccharide units of D-glucuronic acid (GlcUA) and N-acetyl-D-glucosamine (GlcNAc), which are alternately linked, forming a linear polymer.

N-acylurea and O-acyl isourea derivatives for the invention are as shown in the bracketed fragments in the following structural formulas (I) and (II):

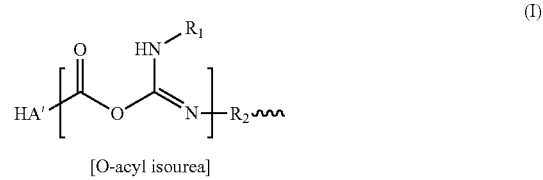

[O-acyl isourea]

(I)

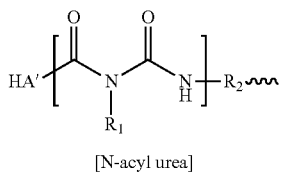

[N-acyl urea]

(II)

In structural formulas (I) and (II), each $R_1$ can be the same or different. Each $R_1$ is selected from the group consisting of hydrogen; substituted or unsubstituted hydrocarbyl groups (linear or branched, or cyclic or acyclic) optionally interrupted by one or more heteroatoms; substituted or unsubstituted alkoxy; substituted or unsubstituted aryloxy; and substituted or unsubstituted aralkyloxy. Examples of substituted or unsubstituted hydrocarbyl groups (linear or branched, or cyclic or acyclic) optionally interrupted by one or more heteroatoms include optionally substituted aliphatic groups (e.g., alkyl, alkenyl, alkynyl, cycloalkyl, cycloalkenyl, cycloalkynyl and cycloaliphaticalkyl); optionally substituted aryl groups (including heteroaryl groups); optionally substituted aliphatic groups interrupted by one or more heteroatoms (e.g., heterocyclyl, cycloaliphaticalkyl and heterocyclylalkyl); and optionally substituted, partially aromatic and partially aliphatic groups (e.g., aralkyl and heteroaralkyl). Suitable optional substituents are those that do not substantially interfere with the properties of the resulting crosslinked HA composition. Suitable substituents for carbon atoms of hydrocarbyl groups include —OH, halogens (—Br, —Cl, —I, —F), —$OR^a$, —O—$COR^a$, —$COR^a$, —CN, —NCS, —$NO_2$, —COOH, —$SO_3H$, —$NH_2$, —$NHR^a$, —$N(R^aR^b)$, —$COOR^a$, —CHO, —$CONH_2$, —$CONHR^a$, —CON$(R^aR^b)$, —$NHCOR^a$, —$NR^bCOR^a$, —$NHCONH_2$, —NH-$CONR^aH$, —$NHCON(R^aR^b)$, —$NR^bCONH_2$, —$NR^bCON$-$R^aH$, —$NR^cCON(R^aR^b)$, —C(=NH)—$NH_2$, —C(=NH)—$NHR^a$, —C(=NH)—$N(R^aR^b)$, —C(=$NR^c$)—$NH_2$, —C(=$NR^c$)—$NHR^a$, —C(=$NR^c$)—$N(R^aR^b)$, —NH—C(=NH)—$NH_2$, —NH—C(=NH)—$NHR^a$, —NH—C(=NH)—$N(R^aR^b)$, —NH—C(=$NR^c$)—$NH_2$, —NH—C(=$NR^c$)—$NHR^a$, —NH—C(=$NR^c$)—$N(R^aR^b)$, —$NR^dH$—C(=NH)—$NH_2$, —$NR^d$—C(=NH)—$N(R^aR^b)$, —$NR^d$—C(=$NR^c$)—$NH_2$, —$NR^d$—C(=$NR^c$)—$NHR^a$, —$NR^d$—C(=$NR^c$)—$N(R^aR^b)$, —$NHNH_2$, —$NHNHR^a$, —$NHR^aR^b$, —$SO_2NH_2$, —$SO_2NHR^a$, —$SO_2NR^aR^b$, —SH, —$SR^a$, —$S(O)R^a$, and —$S(O)_2R^a$. In addition, an alkyl, alkylene, alkenyl or alkenylene group can be substituted with substituted or unsubstituted aryl group to form, for example, an aralkyl group such as benzyl. Similarly, aryl groups can be substituted with a substituted or unsubstituted alkyl or alkenyl group.

$R^a$-$R^d$ are each independently an alkyl group, aryl group, including heteroaryl group, non-aromatic heterocyclic group or —$N(R^aR^b)$, taken together, form a substituted or unsubstituted non-aromatic heterocyclic group. The alkyl, aromatic and non-aromatic heterocyclic group represented by $R^a$-$R^d$ and the non-aromatic heterocyclic group represented by —$N(R^aR^b)$ can optionally be substituted.

In other embodiments, $R_1$ is an optionally substituted aliphatic group (cyclic or acyclic, or linear or branched). More preferably, $R_1$ is an alkyl group, such as C1-C6 alkyl (e.g., methyl, ethyl, propyl, butyl, 2-propyl, tert-butyl, and the like). Preferably, each $R_1$ is ethyl.

Each $R_2$ is independently a substituted or unsubstituted linking group including one or more of hydrocarbylene groups (cyclic or acyclic, or linear or branched) optionally interrupted by one or more heteroatoms. Examples include optionally substituted aliphatic groups (e.g., alkylene, alkenylene, alkynylene, cycloalkylene, cycloalkenylene, cycloalkynylene and cycloaliphaticalkylene); optionally substituted arylene (including heteroaryl groups); optionally substituted aliphatic groups interrupted by one or more heteroatoms (e.g., heterocyclylene, cycloaliphaticalkylene and heterocyclylalkylene); and optionally substituted, partially aromatic and partially aliphatic groups (e.g., aralkylene and heteroaralkylene). Suitable optional substituents are as those described above for $R_1$.

In some embodiments, $R_2$ includes or is interrupted by other groups, e.g, carbonyl, amide, oxy, sulfide, disulfide, and the like. In other embodiments, $R_2$ is a cycloaliphatic, arylene, heteroarylene, or heterocyclylene group. In still other embodiments, $R_2$ is 1,6-hexamethylene, octamethylene, decamethylene, dodecamethylene, PEG, —$CH_2CH_2$—S—S—$CH_2CH_2$—, para-phenylene-S—S-para-phenylene, meta-phenylene-S—S-meta-phenylene, ortho-phenylene-S—S-ortho-phenylene, ortho-phenylene, meta-phenylene or para-phenylene. More preferably, $R_2$ is phenylene. Preferably, $R_2$ is para-phenylene.

In one embodiment, the wavy line connected to $R_2$ in structural formulas (I) and (II) represents hydrogen, substituted or unsubstituted hydrocarbyl groups (linear or branched, or cyclic or acyclic) optionally interrupted by one or more heteroatoms; alkoxy; aryloxy; or aralkyloxy, as described for $R_1$. In another embodiment, the wavy line connected to $R_2$ in structural formulas (I) and (II) represents optionally substituted N-acyl urea group or O-acyl isourea group, as shown below in structural formulas VI-VIII.

In general, the modified HA derivative is prepared by reacting hyaluronic acid, or a salt thereof, with a carbodiimide, preferably a multifunctional carbodiimide, such as a biscarbodiimide, in the absence of a nucleophile or a polyanionic polysaccharide other than HA, to form an N-acylurea or O-acyl isourea.

Examples of suitable carbodiimides in the invention include a monocarbodiimide and a multifunctional carbodiimide, such as a biscarbodiimide. The monocarbodiimide has the formula:

$$R_3-N=C=N-R_4 \qquad (III)$$

wherein $R_3$ and $R_4$ are each independently as described above for $R_1$ (e.g., hydrocarbyl, substituted-hydrocarbyl, alkoxy, aryloxy or alkaryloxy). Examples of suitable monocarbodiimides include: 1-ethyl-3-(3-dimethylaminopropyl)-carbodiimide hydrochloride (EDC); 1-cyclohexyl-3-(2-morpholinoethyl)carbodiimide metho-p-toluenesulfonate (CMC); 1-(3-(dimethylamino)propyl)-3-ethylcarbodiimide methiodide (EAC); 1,3-dicyclohexylcarbodiimide (DCC); and 1-benzyl-3-(3-dimethylaminopropyl) carbodiimide hydrochloride (BDC).

Examples of suitable biscarbodiimides may be represented by those difunctional compounds having the formula:

$$R_1-N=C=N-R_2-N=C=N-R_1 \qquad (IV).$$

Each $R_1$ can be different or the same. $R_1$ and $R_2$ are each independently as described above. Suitable specific examples of biscarbodiimides include 1,6-hexamethylene bis(ethylcarbodiimide), 1,8-octamethylene bis(ethylcarbodiimide), 1,10 decamethylene bis(ethylcarbodiimide), 1,12 dodecamethylene bis(ethylcarbodiimide), PEG-bis(propyl(ethylcarbodiimde)), 2,2'-dithio-bis(ethyl(ethylcarbodiimide)), 1,1'-dithio-ortho-phenylene-bis(ethylcarbodiimide), 1,1'-dithio-para-phenylene-bis(ethylcarbodiimide), and 1,1'-dithio-meta-phenylene bis(ethylcarbodiimide). In a preferred embodiment, the biscarbodiimide is para-phenylene-bis(ethylcarbodiimide). Methods of preparing biscarbodiimides are described, for example, in U.S. Pat. Nos. 6,013,679; 2,946,819; 3,231,610; 3,502,722; 3,644,456; 3,972,933; 4,014,935; 4,066,629; 4,085,140; 4,096,334; 4,137,386, 6,548,081, and 6,620,927 the teachings of which are incorporated herein by reference in their entireties.

In a preferred embodiment, the HA derivative is crosslinked. In a more preferred embodiment, the HA derivative is at least about 1% by mole crosslinked, and the HA derivative includes at least one crosslink, e.g., the linking group connecting through a group U at each end to a HA' molecule, as shown in the following structural formula:

HA'—U—R$_2$—U—HA' (V).

Each HA' in the preceding formula can be different or the same HA' molecule, e.g., the crosslink can be an intermolecular or intramolecular crosslink. Each U can be the same or different and is an optionally substituted N-acyl urea or O-acyl isourea. As used herein, the term "at least about 1% by mole crosslinked" means that HAs are crosslinked with each other via derivatized carboxyl functionalities of the HAs, such as O-acylisoureas or N-acylureas, wherein the derivatized carboxyl functionalities are at least about 1% by mole of the total carboxyl functionalities of the individual HA.

In an even more preferred embodiment, the N-acylurea or O-acylisourea results from crosslinking with the multifunctional carbodiimide. Alternatively, a monocarbodiimide may be employed in combination with a multifunctional carbodiimide. Suitable examples of monocarbodiimides and multifunctional carbodiimides are as described above. Use of a multifunctional carbodiimide to prepare the modified HA derivative causes crosslinking of the hyaluronic acid. For example, use of a biscarbodiimide results in a crosslinking between COOH groups present in the repeating disaccharide unit of hyaluronic acid, since the biscarbodiimide is difunctional. The COOH group may be present in the same polymer chain, resulting in an intramolecular crosslinked product, or present on two different polymer chains, resulting in an intermolecular crosslinked product.

The reaction of HA with a biscarbodiimide rather than a monocarbodiimide does not change the mechanism of reaction, but can cause the product to be crosslinked.

The reaction of HA with a biscarbodiimide crosslinking reagent, in the presence of an available proton, is believed to comprise protonation in the first step. The acid anion can then attach to the carbon atom of the cation formed, resulting in the formation of an O-acyl isourea intermediate. The acyl group in the intermediate can migrate from the oxygen atom to a nitrogen atom to produce a N-acyl isourea derivative of the HA. It is believed that the O-to-N migration can be incomplete, resulting in a product reaction mixture that can include both the N-acyl urea and the O-acyl isourea. Thus, a crosslink resulting from reaction of a biscarbodiimide with the uncrosslinked HA precursor typically can contain two O-acyl isoureas connected through R$_2$, as represented in the following structural formula (VI):

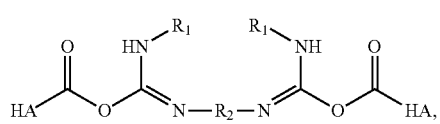

(VI)

or an O-acyl isourea and an N-acyl urea connected through R$_2$, as represented in the following structural formula (VII):

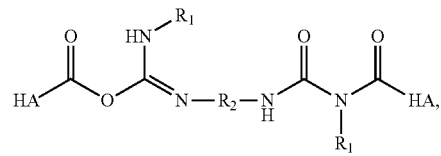

(VII)

or two N-acyl ureas connected through R$_2$, as represented in the following structural formula (VIII):

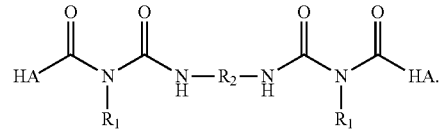

(VIII)

The mixed products can be used separately or together to prepare the compositions according to embodiments of the invention.

The term "hydrocarbyl," as used herein, means a monovalent moiety obtained upon removal of a hydrogen atom from a parent hydrocarbon. As used herein, hydrocarbylene groups are divalent hydrocarbons. Typically, hydrocarbyl and hydrocarbylene groups contain 1-25 carbon atoms, 1-12 carbon atoms or 1-6 carbon atoms. Hydrocarbyl and hydrocarbylene groups can be independently substituted or unsubstituted, cyclic or acyclic, branched or unbranched, and saturated or unsaturated. Optionally, hydrocarbyl and hydrocarbylene groups independently can be interrupted by one or more hetero atoms (e.g., oxygen, sulfur and nitrogen). Examples of hydrocarbyl groups include aliphatic and aryl groups. Substituted hydrocarbyl and hydrocarbylene groups can independently have more than one substituent.

The term "substitutent," as used herein, means a chemical group which replaces a hydrogen atom of a molecule. Representative of such groups are halogen (e.g., —F, —Cl, —Br, —I), amino, nitro, cyano, —OH, alkoxy, alkyl, alkenyl, alkynyl, aryl, haloalkoxy, haloalkyl, haloalkenyl, haloalkynyl, alkyl amino, haloalkyl amino, aryl amido, sulfamido, sulfate, sulfonate, phosphate, phosphino, phosphonate, carboxylate, carboxamido, and the like.

An "alkyl" group, as used herein, is a saturated aliphatic group. The alkyl group can be straight chained or branched, or cyclic or acyclic. Typically, an alkyl group has 1-25 carbon atoms. Examples of alkyl groups include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonodecyl, eicosyl, heneicosyl, docosyl, tricosyl, tetracosyl, pentacosyl, and the isomeric forms thereof. An alkyl group may be substituted with one or more substituents independently selected for each position.

An "alkylene" group, as used herein, is a saturated aliphatic group that is bonded to two other groups each through a single covalent bond. The alkylene group can be straight chained or branched, or cyclic or acyclic. Typically, an alkylene group has 1-25 carbon atoms. Examples of alkylene groups include methylene, ethylene, propylene, butylene, pentylene, hexylene, heptylene, octylene, 1,6-hexamethylene, 1,8-octamethylene, 1,10-decamethylene, 1,12-dodecamethylene and the isomeric forms thereof. An alkylene group may be substituted with one or more substituents independently selected for each position.

As used herein, an "alkenyl" group is an aliphatic group that contains a double bond. Typically, an alkenyl group has 2 to 25 carbon atoms. Examples include vinyl, allyl, butenyl, pentenyl, hexenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, and isomeric forms thereof.

As used herein, an "alkenylene" group is an aliphatic group that contains a double bond. Typically, an alkenylene group has 2 to 25 carbon atoms. Examples include butenylene, pentenylene, hexenylene, octenylene, nonenylene and isomeric forms thereof.

As used herein, an "alkynyl" group is an aliphatic group that contains a triple bond. Typically, an alkynyl group has 2 to 25 carbon atoms. Examples include vinyl, allyl, butynyl, pentynyl, hexynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, and isomeric forms thereof.

As used herein, an "alkynylene" group is an aliphatic group that contains a triple bond. Typically, an alkynylene group has 2 to 25 carbon atoms. Examples include vinylene, allylene, butynylene, pentynylene, hexynylene, octynylene and isomeric forms thereof.

The term "aryl" as used herein refers to an aromatic ring (including heteroaromatic ring). Particularly, an aryl group that includes one or more heteroatoms is herein referred to "heteroaryl." Examples of aryl groups include phenyl, tolyl, xylyl, naphthyl, biphenylyl, triphenylyl, and heteroaryl, such as pyrrolyl, thienyl, furanyl, pyridinyl, oxazolyl, isooxazolyl, thiazolyl, isothiazolyl and quinolinyl. An aryl group may be substituted with one or more substituents independently selected for each position.

The term "arylene" as used herein refers to an aryl ring in a molecule that are bonded to two other groups each through a single covalent bond from two of its ring atoms. Particularly, an arylene group that includes one or more heteroatoms is herein referred to "heteroarylene." Examples of arylene groups include phenylene [—($C_6H_4$)—], such as meta-phenylene and para-phenylene; and heteroarylene groups, such as pyridylene [—($C_5H_3N$)—]; and furanylene [—($C_4H_2O$)—]. An arylene group may be substituted with one or more substituents independently selected for each position.

An alkyl, alkylene, alkenyl, alkenylene group, alkynyl or alkynylene can be optionally substituted with substituted or unsubstituted aryl group to form, for example, an aralkyl group (e.g. benzyl), or aralylene (e.g. —$CH_2$—($C_6H_4$)— or —CH=$CH_2$—($C_6H_4$)—). Similarly, aryl or arylene groups can be optionally substituted with a substituted or unsubstituted alkyl, alkenyl or alkynyl group.

The term "heterocyclyl" refers to a cycloalkyl group wherein one or more ring carbon atoms are replaced with a heteroatom, e.g., aziridyl, azetidyl, pyrrolidyl, piperidyl, thiiranyl, thietanyl, tetrahydrothiophenyl, tetrahydrothiopyranyl, oxiranyl, oxetanyl, tetrahydrofuranyl, tetrahydropyranyl, morpholinyl, and the like.

The term "heterocyclylene" refers to a cycloalkylene group wherein one or more ring carbon atoms are replaced with a heteroatom, e.g., 2,5-tetrahydrofuranylene.

An alkoxy group is an alkyl group connected through an oxygen atom, e.g., methoxy, ethoxy, propoxy and the like.

An aryloxy group is an aryl group connected through an oxygen atom, e.g., phenoxy and the like.

An aralkyloxy group is an aralkyl group connected through an oxygen atom, e.g., benzyl oxy and the like.

In one embodiment, the modified HA derivative is at least about 1% by mole crosslinked. The crosslinked HA gel can be water-soluble or substantially water-insoluble.

In another embodiment, at least about 1% by mole, such as at least about 2% by mole, at least about 5% by mole, or between about 1% by mole and about 20% by mole, of the carboxyl functionalities of the modified hyaluronic acid are derivatized. In yet another embodiment, at least about 25% by mole, such as between about 25% by mole and about 75% by mole, of the derivatized functionalities are O-acylisoureas and/or N-acylureas. In yet another embodiment, the carboxyl functionalities of the modified hyaluronic acid are derivatized, and the derivatized carboxyl functionalities result from crosslinking of HAs with a multifunctional carbodiimide described above, preferably biscarbodiimide. Conditions for such crosslinkings are known in the art, for example, in U.S. Pat. No. 6,548,081, the entire teachings of which are incorporated herein by reference.

The steps required to make a biocompatible HA derivative include providing a sample of HA or a salt thereof, such as sodium hyaluronate. HA from any of a variety of sources, including HA extracted from animal tissues or harvested as a product of bacterial fermentation, can be used as a starting material. Alternatively, the HA used to make the composites of this invention can be produced in commercial quantities by bioprocess technology, as described, for example, in Nimrod et al., PCT Publication No. WO 86/04355.

In one example, the sample of HA or its salt is dissolved in water to make an aqueous solution. In a particular example, the concentration of HA in this first aqueous solution is in the range of between about 0.1% and 5% weight/weight ("w/w"), that is, 1 mg/ml solution to 50 mg/ml solution. In another particular example, the reactions are carried out with a range of about between about 0.4% and 0.6% weight/weight, or 4 to 6 mg of hyaluronic acid per milliliter. The precise concentration used will vary depending on the molecular weight of the HA. At significantly lower concentrations, the reactions are slower and less effective. At significantly higher HA concentrations, the end product may be difficult to handle due to the increase in viscosity. One skilled in the art will be able to determine, with no more than routine experimentation, an acceptable concentration of HA to be used for a particular embodiment. Examples of various acceptable concentrations of HA are described in U.S. Pat. No. 5,356,883, to Kuo et al., the teachings of which are incorporated herein by reference in their entirety.

The pH of the HA solution is then adjusted by the addition of a suitable acid or a suitable pH buffer known in the art, so that the aqueous HA solution is acidic, preferably having a pH of about between 4.0 and 8.0, such as about between 4.0 and about 6.0 or between about pH 4.75 and about pH 5.5. The pH buffer can include any buffer agent known to one skilled in the art, e.g., 2-(N-morpholino)ethanesulfonic acid (MES); 2,2-bis(hydroxymethyl)-2,2',2"-nitrotriethanol; succinate/succinic acid; $KH_2PO_4$; N-tris(hydroxymethyl-2-aminoethanesulfonic acid; triethanolamine; diethylbarbituate; tris(hydroxymethyl)aminoethane; N-tris(hydroxy)methylglycine; and N,N-bis(2-hydroxyethyl)glycine. The buffer agent can be employed with an additional acid or base, e.g., 2-(N-morpholino)ethanesulfonic acid with NaOH; 2,2-bis(hydroxymethyl)-2,2',2"-nitrotriethanol with HCl; succinate with succinic acid; $KH_2PO_4$ with borax; N-tris(hydroxymethyl-2-aminoethanesulfonic acid with NaOH; triethanolamine with HCl; diethylbarbituate with HCl; tris(hydroxymethyl)aminoethane with HCl; N-tris(hydroxy)methylglycine with HCl; and N,N-bis(2-hydroxyethyl)glycine with HCl. Preferably, the buffer includes 2-(N-morpholino) ethanesulfonic acid and NaOH.

Once the pH of the aqueous HA solution has been adjusted, the carbodiimide can be added. Generally an excess of the stoichometric proportion of carbodiimide is advantageous to promote the desired reaction. Preferably the molar equivalent ratio of the carbodiimide to HA is equal to or greater than about 5%.

In one example, the pH of the aqueous HA solution is adjusted by the addition of a suitable acid, such as an HCl solution. Preferably, the carbodiimide is dissolved in an appropriate water-mixable solvent and added drop-wise. In this example, as the carbodiimide and the HA are mixed, the pH of the solution generally increases. Films and gels with various desired physical properties can be obtained by simply allowing the pH to rise as the reaction proceeds. However, the reaction is monitored by a pH meter, and HCl may be added to maintain the pH of the reaction mixture, for example, about between 4.0 and 8.0, such as about between 4.0 and about 6.0 or between about pH 4.75 and about pH 5.5. The reaction is then allowed to proceed at room temperature for about two hours. The reaction may be directed to favor the formation of the N-acylurea derivatives by increasing the pH with a suitable aqueous base. The progress of the reactions described above may be followed by monitoring the pH. When the pH is stabilized, the reactions are substantially complete.

In another example, the carbodiimide, such as biscarbodiimide, is reacted with the HA in the presence of a suitable pH buffer, wherein the buffer is at a pH between about 4 and about 8. Suitable examples of pH buffer agents are as described above. Typically, the buffer agent is mixed in aqueous media, in a concentration between about 5 mM (millimolar) and about 250 mM (e.g., about 75 mM). Typically, the HA is mixed in aqueous media, e.g., the pH buffer solution, in a concentration between about 1 mM (millimolar) and about 100 mM (e.g., about 37 mM). The particular concentration employed can vary depending on the molecular weight of the HA.

The carbodiimide can be combined with the HA solution alone, or more typically as a solution in a water-miscible organic solvent, e.g., acetone, methyl ethyl ketone, dimethyformamide, dimethyl sulfoxide, methanol, ethanol, 2-propanol, acetonitrile, tetrahydrofuran, N-methyl pyrrolidone, and the like. When a biscarbodiimide is utilized, typically, the solvent is acetone, and the biscarbodiimide is at a concentration of between about 0.1 mg/mL and about 100 mg/mL. The HA and the carbodiimide, such as carbodiimide, can be combined in any molar equivalent ratio, e.g., between about 1% and about 200%, typically between about 2% and about 30%. The reaction can be carried out at a temperature range of between about 0° C. and about 60° C., typically between 25-30° C.

Crosslinked HA can be formed by reacting uncrosslinked HA with a crosslinking agent, such as a biscarbodiimide as described above, under suitable reaction conditions by methods known in the art, for example, U.S. patent application Publication Ser. Nos. 10/743,557, U.S. Pat. Nos. 5,356,883, 5,502,081, 6,013,679, 6,537,979, and 6,548,081, the entire teachings of which are incorporated herein by reference. The uncrosslinked HA used as a precursor for the crosslinking typically has typically an average molecular weight range of from between about $6 \times 10^4$ to about $8 \times 10^6$ Daltons, or 150 to 20,000 disaccharide repeat units. Uncrosslinked HA having lower or higher molecular weights than these can also be used in the invention.

The reaction conditions for HA crosslinking with a biscarbodiimide are similar to those used for HA-monocarbodiimide coupling reactions. Advantageously, the crosslinking reactions are carried out with (1) an increase of the HA concentration in the reaction mixture, and/or (2) a decrease of the biscarbodiimide concentration in the addition solution. This creates a condition favorable to intermolecular crosslinking versus intramolecular crosslinking.

At the conclusion of the reactions described above, the desired HA derivative may be separated from the reaction mixtures by conventional methods of precipitation, washing and re-precipitation. The completeness of the reaction, the nature of the products and the extent of chemical modification can be determined by, for example, proton NMR, or by studying the resistance to enzymatic hydrolysis or studying other changes in the physical or chemical behavior of the product.

If a colored product is desired, a solution of a biocompatible dye or stain, e.g., Coomassie™ Brilliant Blue R-250, can be admixed to the reaction mixtures described above. The resulting product will have a blue color which makes the gel, film or sponge easy to see when it is handled during surgery and when it is in place.

When the reaction is complete, sodium chloride is typically added to the reaction mixture to adjust the sodium chloride concentration to 1 M. Ethanol is added to form a precipitate of chemically-modified, HA derivative. The precipitate is separated from the solution, washed, and dried by vacuum. The freeze dried material can be washed with appropriate solvents to remove contaminants of the reaction and dried and then sterilized by ethylene oxide (EtO) sterilization or sterilization by gamma irradiation before loading the cells and implanting them into mammals.

To make a gel of the HA derivative, the precipitate is re-suspended in water and stirred in a cold room. The gel of the HA derivative is a hydrogel. The term "hydrogel" is defined herein to mean a macromolecular network swollen in water or biological fluids. The degree of hydration is dependent on the degree of crosslinking.

The HA derivative can be precipitated by pouring into a water-miscible organic solvent, e.g., acetone, methyl ethyl ketone, dimethyformamide, dimethyl sulfoxide, methanol, ethanol, 2-propanol, acetonitrile, tetrahydrofuran, N-methyl pyrrolidone, and the like, preferably an alcohol, e.g., ethanol. The precipitate can be collected and dried, e.g., under reduced pressure.

The dried HA derivative can be formed into particles by any means well known to one in the art, e.g., abrading, grinding, fracturing, and the like, preferably by grinding in a cryogenic mill. Alternatively, the undried HA derivative can be cryoprecipitated to form small particles, which can then be dried, or the undried crosslinked HA can be ground in a cryogenic mill and then the resulting particles can be dried.

The dried HA derivative can be sterilized using conventional sterilization procedures such as ethylene oxide sterilization, sterilization using irradiation (such as gamma irradiation), hydrogen peroxide sterilization and other such methods know in the art. Alternatively a sterile product can be obtained by using all sterile components and carrying out all reactions and manipulations in under aseptic conditions.

The dehydrated particles are typically hydrated in the presence of the physiologically acceptable solution (e.g., a saline solution, or a phosphate buffer as provided in the Examples).

The HA derivative can be formed as a hydrogel. As the term is used herein, a "hydrogel" is a crosslinked macromolecular network that can swell in water or biological fluids, and can retain a significant portion of water within its structure without dissolving. As used herein, the term "swelling" refers to the taking up of a liquid, for example water, by a gel with an increase in volume, typically with the addition of heat and pressure. Hydrogels have a large molecular weight that generally cannot be measured by conventional methods and are composed of a polymer backbone and crosslinks. To make a hydrogel of the crosslinked HA, the dehydrated particles of the cross-linked HA is typically re-suspended in water or biological fluids. The degree of gelation is dependent on the degree of crosslinking achieved.

The crosslinked HA gel can be water-soluble or substantially water-insoluble. The solubility of the crosslinked HA gel can be tailored by, for example, the degree of the crosslinking. In a preferred embodiment, the HA derivative is crosslinked in a range of between about 1% and 10% in a molar ratio, more preferably about 5% in a molar ratio.

In another aspect of the present invention is a method of treating a subject having a musculoskeletal disorder, including OA, that includes co-administering to the subject an effective amount of an HA derivative as described above or a pharmaceutically acceptable salt thereof, and an effective amount of at least one second bioactive agent other than the HA derivative.

As used herein, "co-administering" includes administering an HA derivative as described above and the second bioactive agent either in a single pharmaceutical composition comprising both, or in separate individual pharmaceutical compositions, wherein the treatment regimen for each drug is independently selected. When administered separately, the HA derivative and the second bioactive agent can be co-administered at the same time, or alternatively, at different times. When the HA derivative and the second bioactive agent are administered at the same time, either in a single pharmaceutical composition comprising both, or in separate individual pharmaceutical compositions, they are administered, for example, weekly in a total of 1-5 (e.g., 1-3, 2-4 and 3-5) times for three, four, five, six or more months' relief. Alternatively, the HA derivative is administered, for example, a total of 1-5 (e.g., 1-3, 2-4 and 3-5) times of weekly injections for three, four, five, six or more months' relief, and the second bioactive agent is administered at different times from those for the HA derivative, for example, a day apart, 2-5 days apart; a week apart; a month apart; or months apart. Alternatively, the HA derivative is administered, for example, weekly in a total of 1-5 (e.g., 1-3, 2-4 and 3-5) times for three, four, five, six or more months' relief, and the second bioactive agent is administered, for example, three times per day; once per day; every week; every month; or every 2-3 months, wherein the treatment regimen for each drug is independently selected.

The second bioactive agent can be any pharmaceutically acceptable cells, nucleic acids, proteins, antibodies, peptides and pharmaceuticals, as long as the second bioactive agent does not interfere the therapeutic activity of the HA derivative of the invention. Examples include agents which are beneficial for the treatment of musculoskeletal disorder. A pharmaceutical, as that term is used herein, includes, for example: compounds and compositions recognized in the official United States Pharmacopoeia, the official Homeopathic Pharmacopoeia of the United States, or the official National Formulary, or any supplement thereof; compounds and compositions intended for use in the diagnosis, cure, mitigation, treatment, or prevention of disease in man or other animals; and compounds and compositions (other than food) intended to affect the structure or any function of the body of man or other animals. Pharmaceuticals include pharmaceutical compounds and solvates, salts, crystal polymorphs, and stereoisomers thereof.

Examples of classes of pharmaceuticals include growth factors/hormones (e.g., interleukins, prostaglandins, thromboxanes, leukotrienes and cytokines), steroidal and non-steroidal, antibiotics, analgesics, anesthetics, barbiturates, aminoalkybenzenes, catecholamines, narcotics, narcotic antagonists, anti-neoplastic agents and anticoagulants (e.g., heparin and heparin sulfate), steroidal and non-steroidal anti-inflammatory drugs, and any synthetic analogues and pharmaceutically-active fragments thereof, and the like. Pharmaceuticals which are suitable for use in embodiments of the invention may be fat soluble, water-soluble, anionic or cationic, as long as they can interact with a group on the hyaluronic aid derivative of an embodiment to form either covalent or ionic bonds or hydrophobic or hydrophilic interactions, for example, a hydrophobic interaction between a pharmaceutical having a hydrophobic moiety and the HA derivative according to an embodiment can occur.

The bioactive agent can be introduced at any stage, but is typically added during preparation of the composition by inclusion in the physiologically compatible solution used to hydrate the dehydrated particles, e.g., a phosphate buffer. In one embodiment, the HA composition, e.g., the hydrated HA particles, includes a steroid.

As used herein, a "physiologically acceptable solution" is any solution known in the art that is useful as a carrier in a physiological system, e.g., aqueous solutions that are typically sterile, non-allergenic, non-toxic, and the like, e.g., a saline solution, a buffer solution, a sugar solution, and the like.

Examples of preferred pharmaceuticals for the invention include growth and differentiation factors/hormones (e.g., BMPs, GDFs, interleukins, prostaglandins, thromboxanes, leukotrienes and cytokines), antibiotics (e.g., penicillin, streptomycin and linocomycin), antifungals, analgesics, anesthetics, steroidal and non-steroidal anti-inflammatory agents, chondroregenerative agents, chondroprotective agents, matrix metalloproteinase (MMP) inhibitors, tissue inhibitors of matrix metalloproteinase (TIMP), bone protective agents, bone regenerating agents, bone anabolic agents, bone resorption inhibitors, and bone osteoclast inhibiting agents, any synthetic analogues and pharmaceutically-active fragments thereof, and the like. Examples of anesthetics, e.g., local anesthetics, include ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dycyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine, and salts thereof.

Preferably, the second bioactive agent can help maintain the integrity of the connective tissues or can provide anti-inflammatory, chondroregenerative or chondroprotective effect. Examples of such second bioactive agent include corticosteroids, and growth and cellular differentiation factors. Other examples include traditional non-steroidal anti-inflammatory drugs (NSAIDs), such as diclofenac sodium, etodolac, indomethacin, ketorolac, sulindac, meclofenamate, nabumetone, pirosicam, flurbiprofen, ibuprofen, ketoprofen, naproxen and oxaprozin. Glucosamine and chondrotin can also be used. Cyclooxygenase (COX) inhibitors, such as COX-2 inhibitors, acetaminophen, opioids, tramadol and capsaicin can also be used. More preferably, the second bioactive agent is a corticosteroid, such as triamcinolone acetonide, triamcinolone hexacetonide, methylprednisolone acetate, Dexamethasone sodium phosphate, betamethasone sodium phosphate, betamethasone acetate, medroxyprogesterone acetate. In another preferred embodiment, uncrosslinked, naturally-occurring hyaluronic acid is used as the second bioactive agent.

In some embodiments, the second bioactive agent is included in an HA composition together with an HA derivative as described above. The second bioactive agent can be admixed with the HA derivative, or alternatively can be introduced during the formation of the HA derivative. For example, the second bioactive agent can be added during preparation of the composition by inclusion in the physiologically compatible solution used to, for example, hydrate the dehydrated HA particles, e.g., the phosphate buffer.

As used herein a subject is a mammal, preferably a human, but can also be an animal in need of veterinary treatment, such as a companion animal (e.g., dogs, cats, and the like), a farm animal (e.g., cows, sheep, pigs, horses, and the like) or a laboratory animal (e.g., rats, mice, guinea pigs, and the like).

An "effective amount" of an HA derivative is a quantity that results in a beneficial clinical outcome of or exerts an influence on, the condition being treated with the HA derivative compared with the absence of treatment. The amount of HA derivative administered to the subject will depend on the degree, severity, and type of the disease or condition, the amount of therapy desired, and the release characteristics of the HA formulation. It will also depend on the subject's health, size, weight, age, sex and tolerance to drugs. In addition, the amount of HA derivative administered to the subject will vary depending upon treatment joints. Typically, a portion of the synovial fluid is removed from an articular site to be treated before the administration of an HA composite of the invention to the articular site. In such a case, the amount of administered volume of an HA composite of the invention is substantially equal to the volume of the synovial fluid removed from the articular site to be treated. Typically, the composition of the invention is administered with sufficient frequency and for a sufficient period of time, to achieve the desired therapeutic effect.

As used herein, an "effective amount" of a second bioactive agent is the amount that is sufficient to have the intended therapeutic effect, e.g., an amount of local anesthetic sufficient to have an anesthetic effect in a subject injected with an HA composition including the agent. One skilled in the art will be able to determine a physiologically effective amount based on the amount of composition employed, the subject's medical history, and the like. The drug concentration can be varied over very broad limits and preferably should be chosen depending on the degree of cross-linking of the HA, the solubility of the drug, its pharmaceutical activity, and the effect desired.

As used herein, the term "treating" refers to administration of the HA derivative of HA composition of the invention that results in a beneficial clinical outcome of, or exerts a positive influence on, the condition being treated.

Typically, the HA derivative or HA composition of the invention is administered to a subject's articular site in need thereof (e.g., an affected joint at the knee, hips, spine, base of thumb, finger, shoulder, ankle and base of the big toe) via an intra-articular injection method known in the art. In the co-therapy of the HA derivative in combination with a second bioactive agent as described above, the second bioactive agent can be administered via an intra-articular injection independently from the HA derivative, or alternatively via other administration methods, depending upon the types of the second bioactive agent.

The HA composition in the invention is a pharmaceutical composition and optionally include one or more of pharmaceutically acceptable carriers and diluents, e.g., aqueous solutions that are typically sterile, non-allergenic, non-toxic, and the like, e.g., a saline solution, a buffer solution, a sugar solution, and the like.

EXEMPLIFICATION

Crosslinked HAs were prepared in the following Examples 1-7 by reacting a biscarbodiimide with uncrosslinked hyaluronic acid in the described ratios. The molecular weight of the uncrosslinked HA used in these examples was approximately from about $5 \times 10^5$ Daltons to about $2 \times 10^6$ Daltons. Uncrosslinked HAs with other molecular weights can also be used to obtain the corresponding crosslinked HAs by the methods described below. The hyaluronic acid used was obtained from rooster combs or bacterial sources.

Example 1

This example illustrates an embodiment of the invention in which a biscarbodiimide, p-phenylene-bis(ethylcarbodiimide), and HA are reacted at a molar equivalent ratio of 16.7%.

A solution of HA (6.0 mg/ml; 1130-ml; 16.9 mequiv) was reacted with a solution of p-phenylene-bis(ethylcarbodiimide) (1 mg/ml in acetone; 302-ml; 1.4 mmol; 2.8 mequiv) according to a procedure described in U.S. Pat. Nos. 5,356,883, 5,502,081, 6,013,679 and 6,548,081, the teachings of which are incorporated herein by reference in their entirety. The precipitate of the cross-linked HA was separated from the solution, washed, and resuspended in saline. The suspension was stirred for 2 days in a cold room to form a water-insoluble gel of about 4 mg/ml concentration. Chloroform equal to ½ of the volume of the aqueous solution was added to the solution and contents were vigorously stirred for seven days in the cold room. The reaction mixture was then centrifuged at 4° C. and 43 k rpm for one hour to remove chloroform. The aqueous/gel layer was aseptically collected and the concentration of sodium chloride in the collected aqueous/gel was adjusted to 1 M. The mixture was stirred for 15 minutes under aseptic conditions. Ethanol equal to 3 volumes of the solution was added to precipitate the cross-linked HA and the precipitate was collected, squeezed to remove ethanol, and shredded into small pieces and dried under aseptic conditions.

Example 2

This example illustrates an embodiment of the invention in which a biscarbodiimide, p-phenylene-bis(ethylcarbodiimide), and HA are reacted at a molar equivalent ratio of 5.0% in MES buffer.

A solution of HA (15.0 mg/ml; 133.3-ml; 4.99 mequiv) in MES buffer (pH 5.5) was reacted with a solution of p-phenylene-bis(ethylcarbodiimide) (15 mg/ml in acetone; 1.8-ml; 0.125 mmol; 0.25 mequiv) according to a procedure described in U.S. Patent Application 2005/0136122 A 1. The reaction mixture was thoroughly mixed (mixing with either a glass rod or an overhead mechanical stirrer, e.g., for ~1 minute, results in a white paste from the clear reaction mixture), and the mixture was allowed to stand at room temperature for about 96 hours. Sodium chloride (6.5 g, to make the mixture 5% by weight of sodium chloride) was mixed into the resulting gel, which was allowed to stand for 1 hour. The crosslinked HA gel was precipitated by addition into about 1.2 L of vigorously stirred ethanol. The precipitate was collected and dried under reduced pressure yielding the crosslinked hyaluronic acid. The dry crosslinked HA precipitate was milled. The powder was packed in a Tyvek®/Mylar® pouch, sealed and sterilized by ethylene oxide (EtO).

Example 3

This example illustrates an embodiment of the invention in which a biscarbodiimide, p-phenylene-bis(ethylcarbodiimide), and HA are reacted at a molar equivalent ratio of 10.0% in MES buffer.

A solution of HA (15.0 mg/ml; 133.3-ml; 4.99 mequiv) in MES buffer (pH 5.5) was reacted with a solution of p-phenylene-bis(ethylcarbodiimide) (15 mg/ml in acetone; 3.6-ml; 0.25 mmol; 0.5 mequiv) according to a procedure described in U.S. Patent Application No. 2005/0136122 A1. The reaction mixture was thoroughly mixed (mixing with either a glass rod or an overhead mechanical stirrer, e.g., for about 1 minute, results in a white paste from the clear reaction mixture), and the mixture was allowed to stand at room temperature for about 96 hours. Sodium chloride (6.5 g, to make the mixture 5% by weight of sodium chloride) was mixed into the resulting gel, which was allowed to stand for 1 hour. The crosslinked HA gel was precipitated by addition into about 1.2 L of vigorously stirred ethanol. The precipitate was collected and dried under reduced pressure yielding the crosslinked hyaluronic acid. The dry crosslinked HA precipitate was milled. The powder was packed in a Tyvek®/Mylar® pouch, sealed and sterilized by ethylene oxide (EtO).

Example 4

This example illustrates an embodiment of the invention in which a biscarbodiimide, p-phenylene-bis(ethylcarbodiimide), and HA are reacted at a molar equivalent ratio of 18.0% in MES buffer.

A solution of HA (15.0 mg/ml; 133.3-ml; 4.99 mequiv) in MES buffer (pH 5.5) was reacted with a solution of p-phenylene-bis(ethylcarbodiimide) (15 mg/ml in acetone; 6.4-ml; 0.45 mmol; 0.9 mequiv) according to a procedure described in U.S. Patent Application 2005/0136122 A1. The reaction mixture was thoroughly mixed (mixing with either a glass rod or an overhead mechanical stirrer, e.g., for about 1 minute, results in a white paste from the clear reaction mixture), and the mixture was allowed to stand at room temperature for about 96 hours. Sodium chloride (6.5 g, to make the mixture 5% by weight of sodium chloride) was mixed into the resulting gel, which was allowed to stand for 1 hour. The crosslinked HA gel was precipitated by addition into about 1.2 L of vigorously stirred ethanol. The precipitate was collected and dried under reduced pressure yielding the crosslinked hyaluronic acid. The dry crosslinked HA precipitate was milled. The powder was packed in a Tyvek®/Mylar® pouch, sealed and sterilized by ethylene oxide.

Example 5

This example illustrates an embodiment of the invention in which sterile solutions of biscarbodiimide, p-phenylene-bis(ethylcarbodiimide), and HA in MES buffer are reacted at a molar equivalent ratio of 5.0% under aseptic conditions.

A solution of sterile HA (5.2 mg/ml; 1000-ml; 13.0 mequiv) in sterile MES buffer (pH 5.5) was reacted with a sterile solution of p-phenylene-bis(ethylcarbodiimide) (2 mg/ml in acetone; 35-ml; 0.33 mmol; 0.66 mequiv) under aseptic conditions at 25° C. The reaction mixture was thoroughly mixed using an overhead mechanical stirrer for 6 hours. The crosslinked HA gel was precipitated by addition into about 6 L of vigorously stirred sterile ethanol. The precipitate was aseptically dried under reduced pressure yielding the sterile crosslinked hyaluronic acid.

Example 6

This example illustrates an embodiment of the invention in which a biscarbodiimide, p-phenylene-bis(ethylcarbodiimide), and HA are reacted at a molar equivalent ratio of 7.5%, with control of the initial pH of the HA solution and the reaction time, and with terminal sterilization of the final product.

A solution of HA in normal saline (as sodium hyaluronate, 10.0 g Na—HA or 25.0 millequivalents) was made up to a concentration of 6 mg/mL. The pH was adjusted to a value of 4.75 by addition of hydrochloric acid. A solution of p-phenylene bis(ethyicarbodiimide) (1 mg/ml in acetone; 200.0 ml; 0.9375 mmol; 1.875 mequiv) was added with rapid stirring. The pH was allowed to rise without further control. The reaction was terminated after 4 hours by the addition of 5 liters of SDA-3A ethanol, which precipitates the crosslinked HA.

The precipitate was isolated, dried under vacuum, and milled to a particle size of less than about 80 μm. The fine, dried particles were then rehydrated by addition of phosphate-buffered saline, and raising the temperature to 60° C. for 24 hours. The final concentration was 22.5 mg crosslinked HA/mL. Four milliliters of the suspension of swelled gel particles was loaded into a 5-mL glass syringe and terminally sterilized by heating in an air-overpressure steam sterilizer.

Example 7

This example illustrates an embodiment of the invention in which a biscarbodiimide, p-phenylene-bis(ethylcarbodiimide), and HA are reacted at a molar equivalent ratio of 7.5%, with control of the pH throughout the reaction and the reaction time, and with terminal sterilization of the final product.

A solution of HA in normal saline (as sodium hyaluronate, 10.0 g Na—HA or 25.0 millequivalents) was made up to a concentration of 6 mg/mL. The pH was adjusted to a value of 6.00 by addition of sodium hydroxide. A solution of p-phenylene bis(ethylcarbodiimide) (1 mg/ml in acetone; 200.0 ml; 0.9375 mmol; 1.875 mequiv) was added with rapid stirring. The pH was maintained at a value of 6.00 by the use of a pH-probe, coupled to a controller and peristaltic pump, controlling the addition of 0.1N HCl. The reaction was terminated after 4 hours by the addition of 5 liters of SDA-3A ethanol, which precipitates the crosslinked HA.

The precipitate was isolated, dried under vacuum, and milled to a particle size of less than about 80 μm. The fine, dried particles were then rehydrated by addition of phosphate-buffered saline, and raising the temperature to 60° C. for 24 hours. The final concentration was 22.5 mg crosslinked HA/mL. The suspension of swelled gel particles was loaded into a 5-mL glass syringe and terminally sterilized by heating in an air-overpressure steam sterilizer.

Example 8

This example illustrates the preparation of a composition of the invention containing crosslinked HA and water insoluble steroid methylprednisolone acetate.

To a 100-mL, 30 mg/mL sterile aqueous suspension of methylprednisolone acetate in phosphate buffer containing Tween®80, 2.25 g sterile crosslinked HA prepared in Example-1-5 were added and the suspension was stirred under aseptic conditions for 24-48 hours. After the complete re-hydration of the crosslinked HA the composition was transferred to sterile syringes making sure that sterility of the composition was not compromised.

Example 9

Prophetic

This example illustrates the preparation of a composition of the invention containing crosslinked HA and water insoluble steroid triamcinolone acetonide.

To a sterile aqueous suspension of triamcinolone acetonide in a buffer containing clinically acceptable excipients, sterile crosslinked HA prepared in Examples 1-7 are added and the suspension is stirred under aseptic conditions for 24-48 hours. A typical concentration of triamcinolone acetonide is 30 mg/mL. A typical concentration of the crosslinked HA is in a range of between about 2 mg/mL and about 30 mg/mL. After the complete re-hydration of the crosslinked HA the composition is transferred to sterile syringes making sure that sterility of the composition is not compromised.

Example 10

Prophetic

This example illustrates the preparation of a composition of the invention containing crosslinked HA and water insoluble steroid betamethasone acetate.

To a sterile aqueous suspension of betamethasone acetate in a buffer containing clinically acceptable excipients, sterile crosslinked HA prepared in Examples 1-7 are added and the suspension is stirred under aseptic conditions for 24-48 hours. A typical concentration of betamethasone acetate is 30 mg/mL. A typical concentration of the crosslinked HA is in a range of between about 2 mg/mL and about 30 mg/mL. After the complete re-hydration of the crosslinked HA the composition is transferred to sterile syringes making sure that sterility of the composition is not compromised.

Example 11

Prophetic

This example illustrates the preparation of a composition of the invention containing crosslinked HA and water soluble steroid betamethasone sodium phosphate.

To a sterile aqueous solution of betamethasone sodium phosphate in a buffer containing clinically acceptable excipients, sterile crosslinked HA prepared in Examples 1-7 are added and the suspension is stirred under aseptic conditions for 24-48 hours. A typical concentration of betamethasone sodium phosphate is 30 mg/mL. A typical concentration of the crosslinked HA is in a range of between about 2 mg/mL and about 30 mg/mL. After the complete re-hydration of the crosslinked HA the composition is transferred to sterile syringes making sure that sterility of the composition is not compromised.

Example 12

Prophetic

This example illustrates the preparation of a composition of the invention containing crosslinked HA and water soluble steroid dexamethasone sodium phosphate.

To a sterile aqueous solution of dexamethasone sodium phosphate in a buffer containing clinically acceptable excipients, sterile crosslinked HA prepared in Example-1-7 are added and the suspension is stirred under aseptic conditions for 24-48 hours. A typical concentration of dexamethasone sodium phosphate is 30 mg/mL. A typical concentration of the crosslinked HA is in a range of between about 2 mg/mL and about 30 mg/mL. After the complete re-hydration of the crosslinked HA the composition is transferred to sterile syringes making sure that sterility of the composition is not compromised.

Example 13

Prophetic

This example illustrates the preparation of a composition of the invention containing crosslinked HA and water-insoluble steroid methylprednisolone acetate (MPA).

After rehydration of the dried crosslinked HA gel suspension described in either Examples 6 or 7, but prior to loading the composition into syringes and sterilizing, 4.44 g of MPA powder are added to the gel suspension (10 mg MPA/mL). The MPA powder is dispersed uniformly in the gel suspension by use of a high-shear mixer. Four milliliters of the gel suspension containing the dispersed MPA is then loaded into 5-mL glass syringe and sterilized as described in Examples 6 and 7.

Example 14

Prophetic

This example illustrates the preparation of a composition of the invention containing crosslinked HA and water-insoluble steroid Triamcinolone acetonide (TMA).

After rehydration of the dried crosslinked HA gel suspension described in either Examples 6 or 7, but prior to loading the composition into syringes and sterilizing, 2.22 g of TMA powder are added to the gel suspension (5 mg TMA/mL). The TMA powder is dispersed uniformly in the gel suspension by use of a high-shear mixer. Four milliliters of the gel suspension containing the dispersed TMA is then loaded into 5-mL glass syringe and sterilized as described in Examples 6 and 7.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A sterile pharmaceutical composition comprising: (a) an effective amount of triamcinolone hexacetonide; and (b) an effective amount of a hyaluronic acid (HA) derivative, wherein the HA derivative is a cross-linked HA gel, wherein the cross-linked HA gel comprises at least one cross-link represented by the following structural formula:

wherein each HA' is a hyaluronic acid that is the same or different;

each U is independently an optionally substituted O-acyl isourea or N-acyl urea;

between about 1% and about 10% by mol of the carboxy functionalities of the HA gel is cross-linked, wherein the composition is formulated for administration as an intra-articular injection, and wherein the composition comprises about 2 mg/mL to about 30 mg/mL of the HA derivative.

2. The composition of claim 1, which provides rapid and prolonged pain relief.

3. The composition of claim 1, which provides pain relief for about 4-6 months.

4. The composition of claim 1, which has been terminally sterilized by steam sterilization.

5. The composition of claim 1, wherein the cross-link is an intermolecular cross-link.

6. The composition of claim 1, wherein the cross-link is an intramolecular cross-link.

7. A syringe comprising the composition of any one of claim 1 or 2-4.

8. The syringe of claim 7, comprising about 4 mL of the composition.

9. The syringe of claim 7, which is a 5-mL syringe.

* * * * *